(12) United States Patent
Yang (10) Patent No.: US 9,945,724 B2
(45) Date of Patent: Apr. 17, 2018

(54) METHOD AND DEVICE FOR DETERMINING YELLOWISH LEVEL OF SCREEN CAUSED BY PRESSING

(71) Applicants: BOE TECHNOLOGY GROUP CO., LTD., Beijing (CN); BEIJING BOE OPTOELECTRONICS TECHNOLOGY CO., LTD., Beijing (CN)

(72) Inventor: Gang Yang, Beijing (CN)

(73) Assignees: BOE TECHNOLOGY GROUP CO., LTD., Beijing (CN); BEIJING BOE OPTOELECTRONICS TECHNOLOGY CO., LTD., Beijing (CN)

(*) Notice: Subject to any disclaimer, the term of this patent is extended or adjusted under 35 U.S.C. 154(b) by 0 days.

(21) Appl. No.: 15/114,644

(22) PCT Filed: Jan. 15, 2016

(86) PCT No.: PCT/CN2016/071029
§ 371 (c)(1),
(2) Date: Jul. 27, 2016

(87) PCT Pub. No.: WO2017/012312
PCT Pub. Date: Jan. 26, 2017

(65) Prior Publication Data
US 2017/0146406 A1 May 25, 2017

(30) Foreign Application Priority Data
Jul. 20, 2015 (CN) .......................... 2015 1 0428977

(51) Int. Cl.
*G01J 3/50* (2006.01)
*G01N 21/25* (2006.01)
(Continued)

(52) U.S. Cl.
CPC ............... *G01J 3/506* (2013.01); *G01J 3/462* (2013.01); *G01N 21/1717* (2013.01);
(Continued)

(58) Field of Classification Search
CPC ...... G01J 2003/467; G01J 3/462; G01J 3/506; G01J 3/46; G01N 21/1717; G01N 21/251;
(Continued)

(56) References Cited

U.S. PATENT DOCUMENTS 5,418,575 A * 5/1995 Kaneko .................... H04N 9/68
348/645
2007/0253008 A1 * 11/2007 Edge .......................... G01J 3/02
358/1.9
(Continued)

FOREIGN PATENT DOCUMENTS

CN 101025880 A 8/2007
CN 101571449 A 11/2009
(Continued)

OTHER PUBLICATIONS

Written Opinion of the International Searching Authority for international application No. PCT/CN2016/071029.

*Primary Examiner* — Gordon J Stock, Jr.
(74) *Attorney, Agent, or Firm* — Harness, Dickey & Pierce, P.L.C.

(57) ABSTRACT

A method and a device for determining a yellowish level of a screen caused by pressing are provided. The method includes: acquiring chromaticity coordinates of a plurality of test points of the screen during a pressing test; processing the acquired chromaticity coordinates, so as to acquire a chromatic aberration between the test point with a maximum value of X or a maximum value of Y in the chromaticity coordinates and the test point with a minimum value of X or a minimum value of Y in the chromaticity coordinates; and (Continued)

comparing the chromatic aberration with a predetermined standard chromatic aberration, so as to determine whether the screen is qualified after the pressing test.

20 Claims, 4 Drawing Sheets

(51) Int. Cl.
  *G01J 3/46* (2006.01)
  *G02F 1/13* (2006.01)
  *G01N 21/17* (2006.01)

(52) U.S. Cl.
  CPC ......... *G01N 21/251* (2013.01); *G02F 1/1309* (2013.01); *G01J 2003/467* (2013.01)

(58) Field of Classification Search
  CPC ............... G01N 21/88; G01N 21/8803; G01N 21/8851; G01N 21/896; G01N 21/9515; G01N 21/958; G01N 21/25; G01N 21/29; G01N 2021/9516; G02F 1/1309; G01M 11/0285; G01M 11/0278; G09G 2320/0242; G09G 2320/029; G09G 2320/0295; G09G 2320/043; G09G 2320/045; G09G 2320/0666

See application file for complete search history.

(56) References Cited

U.S. PATENT DOCUMENTS

| | | | |
|---|---|---|---|
| 2008/0166043 A1* | 7/2008 | Bassi | G09G 3/2003 382/167 |
| 2009/0268036 A1* | 10/2009 | Chou | G09G 3/2007 348/189 |
| 2014/0098258 A1* | 4/2014 | Jia | G09G 5/026 348/224.1 |
| 2014/0232737 A1* | 8/2014 | Zhang | G02B 27/14 345/589 |
| 2014/0267785 A1* | 9/2014 | Chen | H04N 17/02 348/189 |

FOREIGN PATENT DOCUMENTS

| | | |
|---|---|---|
| CN | 101799602 A | 8/2010 |
| CN | 102221554 A | 10/2011 |
| CN | 202093112 U | 12/2011 |
| CN | 102841270 A | 12/2012 |
| CN | 103267630 A | 8/2013 |
| CN | 203323994 U | 12/2013 |
| CN | 103868937 A | 6/2014 |
| CN | 104964745 A | 10/2015 |
| JP | 2004117241 A | 4/2004 |
| JP | 2004251731 A | 9/2004 |
| JP | 2012208852 A | 10/2012 |
| WO | WO-2014-023193 A1 | 2/2014 |

* cited by examiner

| | First Test Point | | Second Test Point | | ...... | | Ninth Test Point | |
|---|---|---|---|---|---|---|---|---|
| | X | Y | X | Y | X | Y | X | Y |
| Initial Chromaticity Coordinates | 0.31 | 0.33 | 0.31 | 0.33 | 0.31 | 0.33 | 0.31 | 0.33 |
| Chromaticity Coordinates (Press 1000 Times) | 0.31 | 0.33 | 0.31 | 0.33 | 0.31 | 0.33 | 0.31 | 0.33 |
| Chromaticity Coordinates (Press 2000 Times) | 0.31 | 0.33 | 0.31 | 0.33 | 0.31 | 0.33 | 0.31 | 0.33 |
| ...... | ...... | | | | | | | |
| Chromaticity Coordinates (Press N thousand Times) | 0.35 | 0.37 | 0.34 | 0.37 | 0.34 | 0.36 | 0.35 | 0.36 |

METHOD AND DEVICE FOR DETERMINING YELLOWISH LEVEL OF SCREEN CAUSED BY PRESSING

CROSS-REFERENCE TO RELATED APPLICATION

This application is the U.S. national phase of PCT Application No. PCT/CN2016/071029 filed on Jan. 15, 2016, which claims a priority of the Chinese Patent Application No. 201510428977.8 filed on Jul. 20, 2015, the disclosures of which are incorporated in their entirety by reference herein.

TECHNICAL FIELD

The present disclosure relates to the field of display technology, in particular to a method for determining a yellowish level of a screen caused by pressing and a device for determining a yellowish level of a screen caused by pressing.

BACKGROUND

Nowadays, a display device of a touch type, such as cell phone or tablet PC, shall be subjected to a pressing test, a clicking test and a lineation test during a factory acceptance test, so as to guarantee that the display device has a sound pressure-resistance and durableness.

During the pressing test, the pillar-like spacers in the display device may be broken after the screen has been pressed for hundreds of thousands of times, so that the liquid crystals may flow to the periphery of the screen. Therefore, the periphery of the screen may be yellowish. In the related art, a yellowish level of a screen is generally tested manually. To be specific, after the pressing test, the worker may determine by eyes whether the screen is yellowish and unqualified.

However, such determination by eyes may be influenced by the individual differences, and thus errors may occur. For example, the operators each may have own determination standard, then a misjudgment, an omission or an over-judgment may occur, thereby reducing an accuracy rate of the determination of the yellowish level of the screen.

SUMMARY

An objective of the present disclosure is to provide a method for determining a yellowish level of a screen caused by pressing, so as to improve the accuracy rate of determining the yellowish level of the screen.

To achieve this objective, a method for determining a yellowish level of a screen caused by pressing is provided, including: acquiring chromaticity coordinates of a plurality of test points of the screen during a pressing test; processing the acquired chromaticity coordinates, so as to acquire a chromatic aberration between the test point with a maximum value of X or a maximum value of Y in the chromaticity coordinates and the test point with a minimum value of X or a minimum value of Y in the chromaticity coordinates; and comparing the chromatic aberration with a predetermined standard chromatic aberration, so as to determine whether the screen is qualified after the pressing test.

According to the method for determining a yellowish level of a screen caused by pressing, the chromaticity coordinates of the plurality of test points of the screen during the pressing test are acquired, and then the acquired chromaticity coordinates are processed, so as to acquire the chromatic aberration between the test point with a maximum value of X or a maximum value of Y in the chromaticity coordinates and the test point with a minimum value of X or a minimum value of Y in the chromaticity coordinates; and then the chromatic aberration is compared with the predetermined standard chromatic aberration, so as to determine whether the screen is qualified after the pressing test.

According to the method of determining a yellowish level of a screen caused by pressing of the present disclosure, it is able to avoid the misjudgment, the omission or the over-judgment, thereby improving an accuracy rate of determining the yellowish level of the screen in compared with the detection merely using human eyes.

The present disclosure further provides in some embodiments a device for determining a yellowish level of a screen caused by pressing, including: an acquisition module, configured to acquire chromaticity coordinates of a plurality of test points of the screen during a pressing test; a processing module, configured to process the acquired chromaticity coordinates, so as to acquire a chromatic aberration between the test point with a maximum value of X or a maximum value of Y in the chromaticity coordinates and the test point with a minimum value of X or a minimum value of Y in the chromaticity coordinates; and a determination module, configured to compare the chromatic aberration with a predetermined standard chromatic aberration, so as to determine whether the screen is qualified after the pressing test.

According to the device for determining a yellowish level of a screen caused by pressing, the acquisition module is configured to acquire chromaticity coordinates of the plurality of test points of the screen during the pressing test and then sends the chromaticity coordinates to the processing module. The processing module is configured to process the acquired chromaticity coordinates, so as to acquire the chromatic aberration between the test point with the maximum value of X or the maximum value of Y in the chromaticity coordinates and the test point with the minimum value of X or the minimum value of Y in the chromaticity coordinates and then sends the chromatic aberration to the determination module. The determination module is configured to compare the chromatic aberration with the predetermined standard chromatic aberration, so as to determine whether the screen is qualified after the pressing test. Compared with the related art, it is able for the device according to the present disclosure to determine accurately whether the screen is qualified after the pressing test by the cooperation of the acquisition module, the processing module and the determination module, thereby avoiding the misjudgment, the omission or the over-judgment caused during the detection merely using human eyes and then improving an accuracy rate of the determination of the yellowish level of the screen.

DETAILED DESCRIPTION

In order to make the objects, the technical solutions and the advantages of the present disclosure more apparent, the present disclosure will be described hereinafter in a clear and complete manner in conjunction with the drawings and embodiments. Obviously, the following embodiments merely relate to a part of, rather than all of, the embodiments of the present disclosure, and based on these embodiments, a person skilled in the art may obtain the other embodiments, which also fall within the scope of the present disclosure.

Unless otherwise defined, any technical or scientific term used herein shall have the common meaning understood by a person of ordinary skills. Such words as "first" and "second" used in the specification and claims are merely used to differentiate different components rather than to represent any order, number or importance. Similarly, such words as "one" or "one of" are merely used to represent the existence of at least one member, rather than to limit the number thereof. Such words as "connect" or "connected to" may include electrical connection, direct or indirect, rather than to be limited to physical or mechanical connection. Such words as "on", "under", "left" and "right" are merely used to represent relative position relationship, and when an absolute position of the object is changed, the relative position relationship will be changed too.

In order to facilitate the understanding, a method and a device for determining a yellowish level of a screen caused by pressing will be described hereinafter in details in conjunction with the drawings.

Figure 1A:
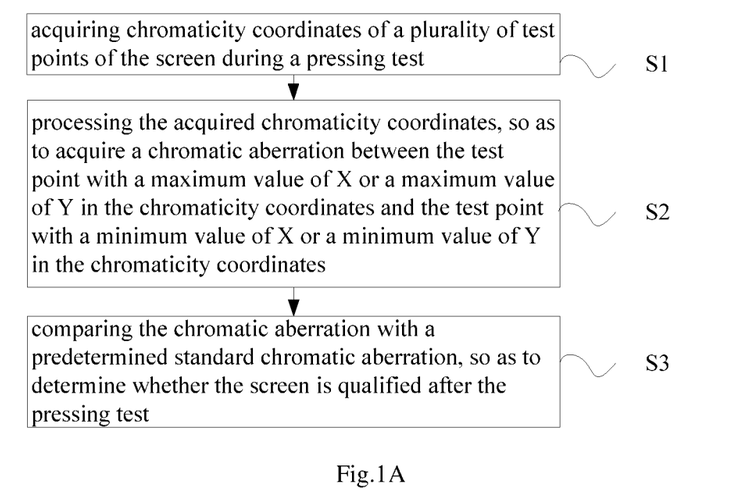
FIGS. 1A-1C are flow charts illustrating a method for determining a yellowish level of a screen caused by pressing in some embodiments of the present disclosure.

A method for determining a yellowish level of a screen caused by pressing is provided in some embodiments of the present disclosure. As shown in FIG. 1, the method includes the following steps.

Step S1: acquiring chromaticity coordinates of a plurality of test points of the screen during a pressing test.

The chromaticity coordinates hereinabove refers to the chromaticity coordinates of a point in a chromaticity diagram which has a color identical to a certain test point in the screen. A color is generally represented by chromaticity coordinates (X, Y) in colorimetry. For example, the chromaticity coordinates of the standard red is (0.67,0.33), the chromaticity coordinates of the standard green is (0.21, 0.71), the chromaticity coordinates of the standard blue is (0.14,0.08), and the chromaticity coordinates of the pure white is (0.33, 0.33).

It should be understood by those skilled in the art that, the chromaticity coordinates hereinabove refers to the chromaticity coordinates of the light emitted from the test point after being lightened. The chromaticity coordinates of the plurality of test points may be acquired at one time or multiple times.

Step S2: processing the acquired chromaticity coordinates, so as to acquire a chromatic aberration between the test point with a maximum value of X or a maximum value of Y in the chromaticity coordinates and the test point with a minimum value of X or a minimum value of Y in the chromaticity coordinates. Such processing may be performed by a processing module.

Step S3: comparing the chromatic aberration with a predetermined standard chromatic aberration, so as to determine whether the screen is qualified after the pressing test. To be specific, when the chromatic aberration is not greater than the predetermined standard chromatic aberration, it is determined that the screen is qualified after the pressing test. When the chromatic aberration is greater than the predetermined standard chromatic aberration, it is determined that the screen is unqualified after the pressing test. Such determination may be performed by a determination module. According to the method for determining a yellowish level of a screen caused by pressing in the embodiment, the chromaticity coordinates of a plurality of test points of the screen during a pressing test are acquired, and then the acquired chromaticity coordinates are processed, so as to acquire a chromatic aberration between the test point with a maximum value of X or a maximum value of Y in the chromaticity coordinates and the test point with a minimum value of X or a minimum value of Y in the chromaticity coordinates; and then the chromatic aberration is compared with the predetermined standard chromatic aberration, so as to determine whether the screen is qualified after the pressing test. According to the method for determining a yellowish level of a screen caused by pressing of the present disclosure, it is able to avoid misjudgment, omission or over-judgment, thereby improving an accuracy rate of determining the yellowish level of the screen, compared with the detection merely using human eyes.

Figure 1B:
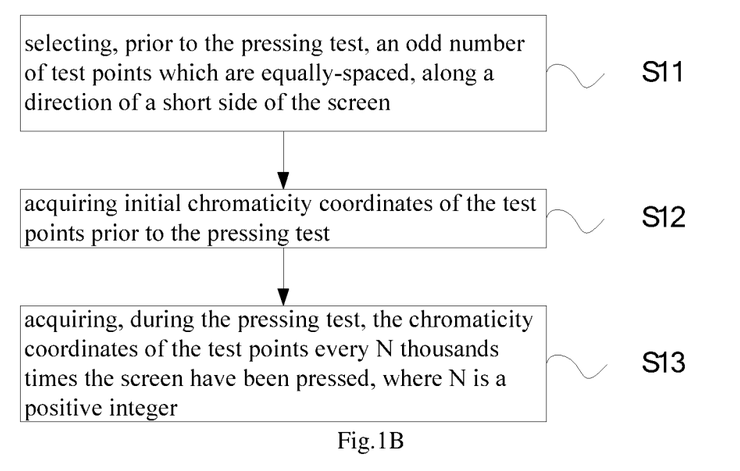

In the practical application, as shown in FIG. 1B, the above Step S1 may further include the following steps.

Figure 2A:
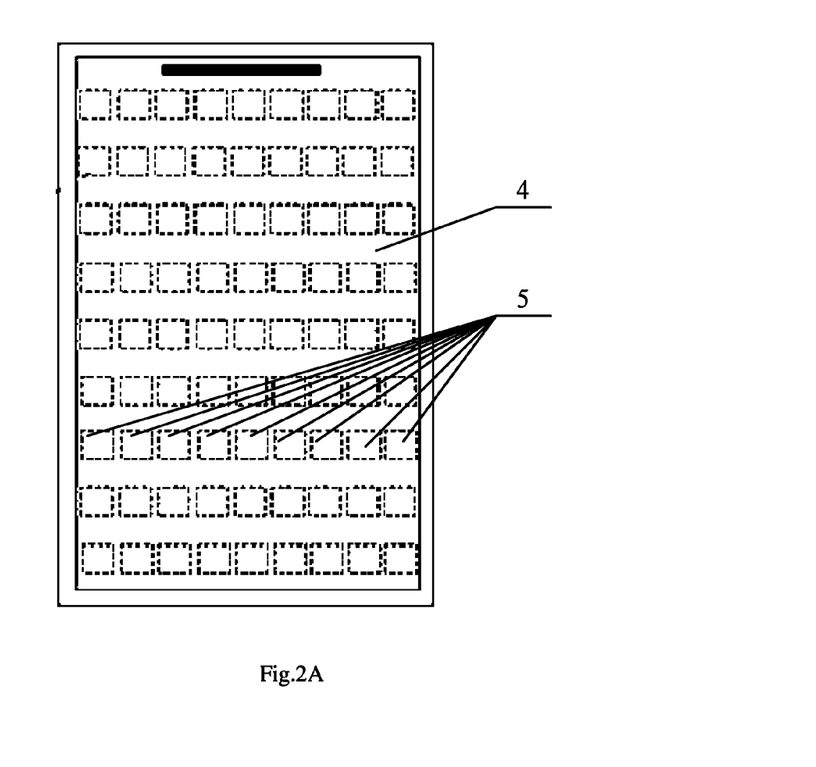
FIGS. 2A-2D are schematic views illustrating a method for determining a yellowish level of a screen caused by pressing in some embodiments of the present disclosure.

Step S11: selecting, prior to the pressing test, an odd number of test points which are equally-spaced, along a direction of a short side of the screen. As shown in FIG. 2A, nine test points 5, which are equally-spaced, are selected along a direction of a short side of the screen 4 prior to the pressing test, such as the dashed boxes in the third row from the bottom.

Step S12: acquiring initial chromaticity coordinates of the test points prior to the pressing test.

Step S13: acquiring, during the pressing test, the chromaticity coordinates of the test points every N thousands times the screen have been pressed, where N is a positive integer such as "1".

Figure 2B:
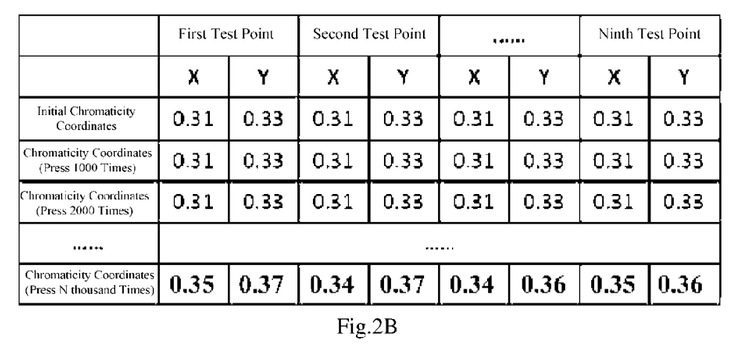

As shown in FIG. 2B, in Step S12 and Step S13, initial chromaticity coordinates of the test points 5 are acquired prior to the pressing test, and during the pressing test, the chromaticity coordinates of the test points 5 are acquired every one thousand times the screen 4 have been pressed.

To be specific, in order to improve the accuracy of the determination of the yellowish level of the screen 4 caused by pressing, prior to the pressing test, a plurality of groups of test points 5 may be selected along a direction of a long side of the screen 4, such as the nine groups of dashed boxes from top down shown in FIG. 2A.

Figure 1C:
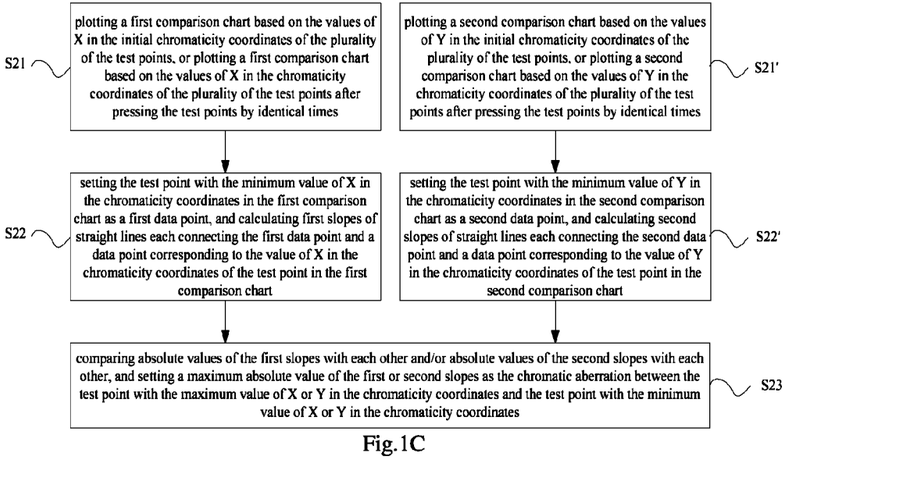

As shown in FIG. 1C, in order to acquire, more accurately, the chromatic aberration between the test point with the maximum value of X or the maximum value of Y in the chromaticity coordinates and the test point with the minimum value of X or the minimum value of Y in the chromaticity coordinates, the Step S2 hereinabove may further include the following steps.

Step S21: plotting a first comparison chart based on the values of X in the initial chromaticity coordinates of the plurality of the test points, or plotting a first comparison chart based on the values of X in the chromaticity coordinates of the plurality of the test points after pressing the test points by identical times.

Step S21': plotting a second comparison chart based on the values of Y in the initial chromaticity coordinates of the plurality of the test points, or plotting a second comparison chart based on the values of Y in the chromaticity coordinates of the plurality of the test points after pressing the test points by identical times.

Figure 2C:
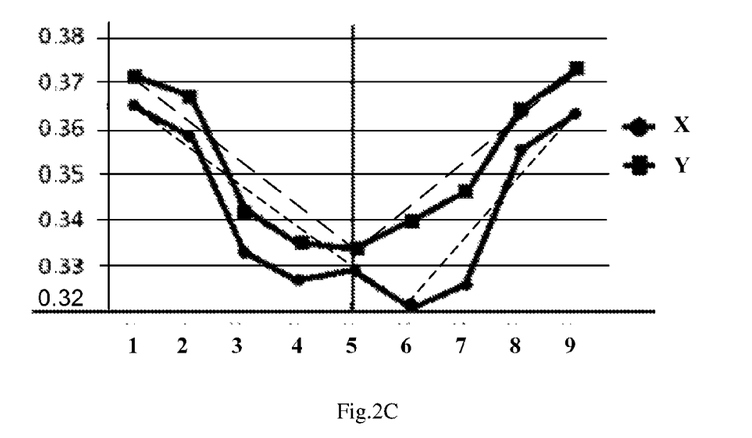

As shown in FIG. 2C, in Step S21 and Step S21', the comparison chart is plotted based on the values of X or Y in the initial chromaticity coordinates of the nine test points 5 (this comparison chart is plotted by combining the first and the second comparison charts), or plotted based on the values of X or Y in the chromaticity coordinates of the nine test points 5 after pressing the test points 5 by identical times. For example, FIG. 2C may be a comparison chart which is plotted based on the values of X and Y in the chromaticity coordinates of the nine test points 5 after pressing the test points 5 for 5000 times.

In the first comparison chart, names of the test points are indicated by a horizontal axis, one coordinate unit represents a distance between two adjacent test points. The coordinates on the horizontal axis indicate a first, a second, a third an $n^{th}$ test point respectively (n=9 in FIG. 2C). The values of X in the chromaticity coordinates of the test points are indicate by a vertical axis of the first comparison chart. Similarly, the second comparison chart is integrated in FIG. 2C, so the horizontal axis hereinabove is also applicable to the second comparison chart, where the values of Y in the chromaticity coordinates of the test points are indicated by the vertical axis.

Step S22: setting the test point with the minimum value of X in the chromaticity coordinates in the first comparison chart as a first data point, and calculating first slopes of straight lines each connecting the first data point and a data point corresponding to the value of X in the chromaticity coordinates of the test point in the first comparison chart. To be specific, in the combined comparison chart, the names of the test points are indicated by the horizontal axis, and the values of X of the chromaticity coordinates are indicated by the vertical axis. The test point with the minimum value of X in the chromaticity coordinates is generally arranged in the middle along the direction of the short side of the screen. The reason is that, the test points, which are arranged in the middle along the direction of the short side of the screen, are often selected for the test, so the portion of the screen at the position corresponding to the test points are subjected to a largest pressure and thus a largest deformation are formed therein and a least quantity of liquid crystals are left, and thus the colors corresponding to the chromaticity coordinates thereof are bluish. Of course, the test point with the minimum value of X in the chromaticity coordinates may be other test points, as shown in FIG. 2C.

Step S22': setting the test point with the minimum value of Y in the chromaticity coordinates in the second comparison chart as a second data point, and calculating second slopes of straight lines each connecting the second data point and a data point corresponding to the value of Y in the chromaticity coordinates of the test point in the second comparison chart. To be specific, in the combined comparison chart, the names of the test points are indicated by the horizontal axis, and the values of Y of the chromaticity coordinates are indicated by the vertical axis.

As shown in FIG. 2C, in Step S22 and Step S22', the value of X in the chromaticity coordinates of the test point 5 in the middle of the screen 4 along the direction of the short side of the screen 4 is set as the first data point, and the value of Y thereof is set as the second data point. In the combined comparison chart, the first slopes of the straight lines each connecting the first data point and a data point corresponding to the value of X in the chromaticity coordinates of the test point 5 are calculated, and the second slopes of the straight lines each connecting the second data point and a data point corresponding to the value of Y in the chromaticity coordinates of the test point 5 are calculated. Because the test points 5 at two sides of the screen 4 along the direction of the short side of the screen 4 are generally with relatively larger chromaticity coordinates, merely four dashed lines with the first and second slopes are shown in FIG. 2C, so as to highlight the high yellowish level of the screen 4.

As shown in FIG. 1C, the Step S2 hereinabove may further include Step S23 of comparing absolute values of the first slopes with each other and/or absolute values of the second slopes with each other, and set a maximum absolute value of the first or second slopes as the chromatic aberration between the test point with the maximum value of X or Y in the chromaticity coordinates and the test point with the minimum value of X or Y in the chromaticity coordinates. As shown in FIG. 2C, the absolute values of the two first slopes are compared with each other, and the absolute values of the two second slopes are compared with each other, and then the maximum absolute value of the first or second slopes is set as the chromatic aberration between the test point 5 with the maximum value of X or Y in the chromaticity coordinates and the test point 5 with the minimum value of X or Y in the chromaticity coordinates. To facilitate the description, the slopes hereinafter will refer to the absolute values of the slopes.

Figure 2D:
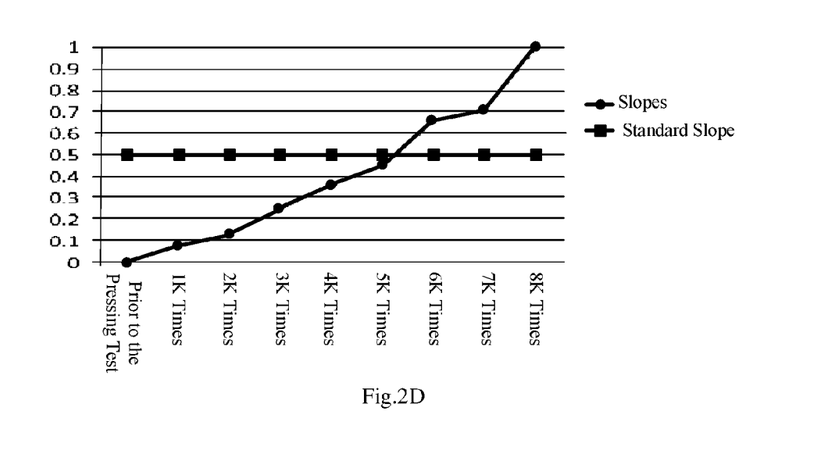

As shown in FIG. 2D, in Step S3 hereinabove, the calculated maximum first and/or second slopes are compared with the predetermined standard chromatic aberration. In the present disclosure, the predetermined standard chromatic aberration may be set as 0.5. The first slopes and/or the second slopes every certain times the screen has been pressed are shown in FIG. 2D. When the maximum first and/or the second slopes are not greater than the standard chromatic aberration, it is determined that the screen is qualified after the pressing test. For example, as shown in FIG. 2D, the screen 4 is still qualified after being pressed by 5000 times. However, the screen 4 will be unqualified very soon if the pressing continues.

In order to further determine the yellowish level of the screen of the qualified product, the determining method hereinabove may further include: for the screen which is qualified after the pressing test, dividing the chromatic aberration by the predetermined standard chromatic aberration to acquire a quotient, and determining a yellowish level of the screen based on the resultant quotient. The yellowish level of the screen is in direct proportion to the resultant quotient.

The determining method hereinabove is merely one of some embodiments of the present disclosure, and the yellowish level of the screen may further be determined based on a curvature of a parabola plotted by connecting the chromaticity coordinates of the test points, which is similar to the principle of determining the yellowish level based on the slopes hereinabove. For example, the method may include: acquiring chromaticity coordinates of a plurality of test points of the screen during a pressing test; processing the acquired chromaticity coordinates, so as to acquire a curvature of a test point with the maximum value of X or Y; comparing the curvature with the standard chromatic aberration; and determining that the screen is qualified after the pressing test in the case that the curvature is not greater than the standard chromatic aberration. It can be seen that, the chromatic aberration in some embodiments of the present disclosure is not limited to the slope and the curvature.

To be specific, a comparison chart is plotted based on the values of X or Y in the initial chromaticity coordinates of the plurality of the test points, or a comparison chart is plotted based on the values of X or Y in the chromaticity coordinates of the plurality of the test points after pressing the test points by identical times. Names of the test points are indicated by a horizontal axis of the comparison chart. One coordinate unit represents a distance between two adjacent test points. The values of X or Y in the chromaticity coordinates of the test points are indicated by a vertical axis of the comparison chart. A parabola is plotted by connecting data points corresponding to the values of X or Y in the chromaticity coordinates of the test points in the comparison chart, so that each data point in the parabola has a corresponding curvature.

In addition, a test point 5 may be selected along a direction of a long side of the screen 4, and chromaticity coordinates of the test point 5 are acquired every certain times the screen has been pressed, and then the acquired chromaticity coordinates are compared with the standard chromatic aberration, so as to determine whether the screen is qualified after the pressing test.

Figure 3:
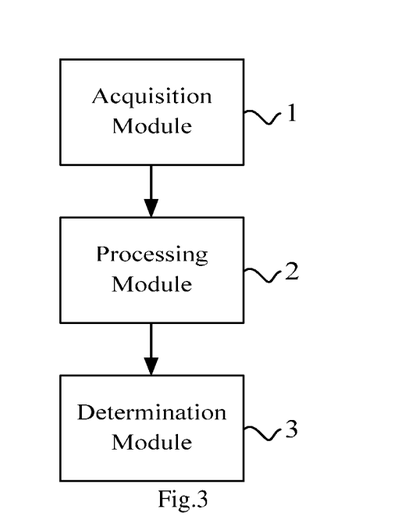
FIG. 3 is a schematic view showing modules of a device for determining a yellowish level of a screen caused by pressing in some embodiments of the present disclosure.

A device for determining a yellowish level of a screen caused by pressing is provided in some embodiments of the present disclosure. As shown in FIG. 3, the device includes: an acquisition module 1, configured to acquire chromaticity coordinates of a plurality of test points of the screen during a pressing test; a processing module 2, configured to process the acquired chromaticity coordinates, so as to acquire a chromatic aberration between the test point with a maximum value of X or a maximum value of Y in the chromaticity coordinates and the test point with a minimum value of X or a minimum value of Y in the chromaticity coordinates; and a determination module 3, configured to compare the chromatic aberration with a predetermined standard chromatic aberration, so as to determine whether the screen is qualified after the pressing test.

In some embodiments of the present disclosure, the acquisition module may be an optical test lens, and the processing module and the determination module may be central processing units and so on.

According to the device for determining a yellowish level of a screen caused by pressing of the present disclosure, the acquisition module 1 is configured to acquire chromaticity coordinates of a plurality of test points 5 of the screen 4 during a pressing test and then send the chromaticity coordinates to the processing module 2. The processing module 2 is configured to process the acquired chromaticity coordinates, so as to acquire the chromatic aberration between the test point 5 with the maximum value of X or the maximum value of Y in the chromaticity coordinates and the test point 5 with the minimum value of X or the minimum value of Y in the chromaticity coordinates and then send the chromatic aberration to the determination module 3. The determination module 3 is configured to compare the chromatic aberration with the predetermined standard chromatic aberration, so as to determine whether the screen 4 is qualified after the pressing test. Compared with the related art, according to the device for determining the yellowish level of the screen caused by pressing of the present disclosure, it is able to determine accurately whether the screen 4 is qualified after the pressing test by the cooperation of the acquisition module 1, the processing module 2 and the determination module 3, thereby avoiding misjudgment, omission or over-judgment caused during the detection merely using human eyes, and then improving the accuracy rate of the determination of the yellowish level of the screen.

Figure 4:
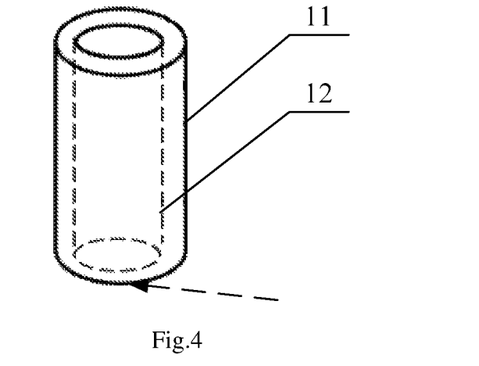
FIG. 4 is a schematic view showing a device for determining a yellowish level of a screen caused by pressing in some embodiments of the present disclosure.

As shown in FIG. 4, the device for determining a yellowish level of a screen caused by pressing may further include: a pressure application mechanism 11, configured to perform the pressing test on the screen 4; and an optical test lens 12 arranged in the pressure application mechanism 11 and configured to acquire the chromaticity coordinates of the test points 5 of the screen 4. To be specific, the optical test lens 12 may adopt the lens used in the display color analyzer CA-210, and may have a better test precision and rate than the CA-210. Therefore, during the pressing test, the acquisition module 1 may acquire at any time the chromaticity coordinates of the test point 5 of the screen 4 below the pressure application mechanism 11 by the optical test lens 12 in the device, and then send the acquired chromaticity coordinates to the processing module 2.

In order to improve the accuracy of the device, the pressure application end (indicated by the dashed arrow in FIG. 4) of the pressure application mechanism 11 may be made of optical abrasion-resistant glass, so that the pressing test may be performed normally and the optical test lens 12 in the pressure application mechanism 11 may have a good optical test effect.

According to the method and device for determining a yellowish level of a screen caused by pressing, compared with the related art where the determination is made by human eyes, it is able to perform the determination timely after the pressing test and determine the times by which the screen has been pressed when the screen is determined to be unqualified due to yellowish. According to the method and device for determining a yellowish level of a screen caused by pressing, it is able to determine effectively the yellowish level of the periphery portion of the screen during the pressing test, so as to avoid errors and delays caused during the determination made by human eyes. Besides, the method and device of the present disclosure are simpler and easier to be implemented.

The above are merely the preferred embodiments of the present disclosure. A person skilled in the art may make further replacements and improvements without departing from the principle of the present disclosure, and these replacements and improvements shall also fall within the scope of the present disclosure.

What is claimed is:

1. A method for determining a yellowish level of a screen caused by pressing, comprising:
   acquiring chromaticity coordinates of a plurality of test points of the screen during a pressing test;
   processing the acquired chromaticity coordinates, so as to acquire a chromatic aberration between the test point with a maximum value of X or a maximum value of Y in the chromaticity coordinates and the test point with a minimum value of X or a minimum value of Y in the chromaticity coordinates; and
   comparing the chromatic aberration with a predetermined standard chromatic aberration, so as to determine whether the screen is qualified after the pressing test.

2. The method according to claim 1, wherein the step of acquiring chromaticity coordinates of a plurality of test points of the screen during a pressing test comprises:
   selecting, prior to the pressing test, an odd number of test points which are equally-spaced, along a direction of a short side of the screen;
   acquiring initial chromaticity coordinates of the test points prior to the pressing test; and acquiring, during the pressing test, the chromaticity coordinates of the test points every N thousands times the screen have been pressed, wherein N is a positive integer.

3. The method according to claim 2, wherein the step of processing the chromaticity coordinates so as to acquire a chromatic aberration between the test point with a maximum value of X or a maximum value of Y in the chromaticity coordinates and the test point with a minimum value of X or a minimum value of Y in the chromaticity coordinates comprises:

plotting a first comparison chart based on the values of X in the initial chromaticity coordinates of the plurality of the test points, or plotting a first comparison chart based on the values of X in the chromaticity coordinates of the plurality of the test points after pressing the test points by identical times, wherein names of the test points are indicated by a horizontal axis of the first comparison chart, one coordinate unit represents a distance between two adjacent test points, and the values of X in the chromaticity coordinates of the test points are indicated by a vertical axis of the first comparison chart;

setting the test point with the minimum value of X in the chromaticity coordinates in the first comparison chart as a first data point;

calculating first slopes of straight lines each connecting the first data point and a data point corresponding to the value of X in the chromaticity coordinates of the test point in the first comparison chart; and comparing absolute values of the first slopes with each other, and setting a maximum absolute value of the first slopes as the chromatic aberration between the test point with the maximum value of X in the chromaticity coordinates and the test point with the minimum value of X in the chromaticity coordinates.

4. The method according to claim 3, wherein the step of processing the chromaticity coordinates so as to acquire a chromatic aberration between the test point with a maximum value of X or a maximum value of Y in the chromaticity coordinates and the test point with a minimum value of X or a minimum value of Y in the chromaticity coordinates comprises:

plotting a second comparison chart based on the values of Y in the initial chromaticity coordinates of the plurality of the test points, or plotting a second comparison chart based on the values of Y in the chromaticity coordinates of the plurality of the test points after pressing the test points by identical times, wherein names of the test points are indicated by a horizontal axis of the second comparison chart, one coordinate unit represents a distance between two adjacent test points, and the values of Y in the chromaticity coordinates of the test points are indicated by a vertical axis of the second comparison chart;

setting the test point with the minimum value of Y in the chromaticity coordinates in the second comparison chart as a second data point;

calculating second slopes of straight lines each connecting the second data point and a data point corresponding to the value of Y in the chromaticity coordinates of the test point in the second comparison chart; and comparing absolute values of the second slopes with each other, and setting a maximum absolute value of the second slopes as the chromatic aberration between the test point with the maximum value of Y in the chromaticity coordinates and the test point with the minimum value of Y in the chromaticity coordinates.

5. The method according to claim 4, wherein the step of comparing the chromatic aberration with a predetermined standard chromatic aberration, so as to determine whether the screen is qualified after the pressing test comprises comparing the maximum absolute value of the first slopes with the predetermined standard chromatic aberration, and determining that the screen is qualified after the pressing test in the case that the maximum absolute value of the first slopes is not greater than the predetermined standard chromatic aberration; and/or comparing the maximum absolute value of the second slopes with the predetermined standard chromatic aberration, and determining that the screen is qualified after the pressing test in the case that the maximum absolute value of the second slopes is not greater than the predetermined standard chromatic aberration.

6. The method according to claim 2, wherein the step of processing the chromaticity coordinates so as to acquire a chromatic aberration between the test point with a maximum value of X or a maximum value of Y in the chromaticity coordinates and the test point with a minimum value of X or a minimum value of Y in the chromaticity coordinates comprises:

plotting a first comparison chart based on the values of X in the initial chromaticity coordinates of the plurality of the test points, or plotting a first comparison chart based on the values of X in the chromaticity coordinates of the plurality of the test points after pressing the test points by identical times, wherein names of the test points are indicated by a horizontal axis of the first comparison chart, one coordinate unit represents a distance between two adjacent test points, and the values of X in the chromaticity coordinates of the test points are indicated by a vertical axis of the first comparison chart;

plotting a parabola by connecting data points corresponding to the values of X in the chromaticity coordinates of the test points in the first comparison chart, so that each data point in the parabola has a corresponding curvature; and calculating a first curvature of the test point with the maximum value of X in the chromaticity coordinates, and setting the first curvature as the chromatic aberration.

7. The method according to claim 6, wherein the step of processing the chromaticity coordinates so as to acquire a chromatic aberration between the test point with a maximum value of X or a maximum value of Y in the chromaticity coordinates and the test point with a minimum value of X or a minimum value of Y in the chromaticity coordinates comprises:

plotting a second comparison chart based on the values of Y in the initial chromaticity coordinates of the plurality of the test points, or plotting a second comparison chart based on the values of Y in the chromaticity coordinates of the plurality of the test points after pressing the test points by identical times, wherein names of the test points are indicated by a horizontal axis of the second comparison chart, one coordinate unit represents a distance between two adjacent test points, and the values of Y in the chromaticity coordinates of the test points are indicated by a vertical axis of the second comparison chart;

plotting a parabola by connecting data points corresponding to the values of Y in the chromaticity coordinates of the test points in the second comparison chart, so that each data point in the parabola has a corresponding curvature; and calculating a second curvature of the test point with the maximal value of Y in the chromaticity coordinates, and setting the second curvature as the chromatic aberration.

8. The method according to claim 7, wherein the step of comparing the chromatic aberration with a predetermined standard chromatic aberration, so as to determine whether the screen is qualified after the pressing test comprises:

comparing the first or the second curvature with the predetermined standard chromatic aberration, and determining that the screen is qualified after the pressing test in the case that neither of the first and the second curvatures is greater than the predetermined standard chromatic aberration.

9. The method according to claim 5, further comprising:

for the screen which is qualified after the pressing test, dividing the chromatic aberration by the predetermined standard chromatic aberration to acquire a resultant quotient; and determining a yellowish level of the screen based on the resultant quotient.

10. The method according to claim 8, further comprising:

for the screen which is qualified after the pressing test, dividing the chromatic aberration by the predetermined standard chromatic aberration to acquire a resultant quotient; and determining a yellowish level of the screen based on the resultant quotient.

11. The method of claim 1, wherein:

the acquiring chromaticity coordinates of a plurality of test points of the screen during a pressing test includes acquiring, by an optical test lens, the chromaticity coordinates of the plurality of test points of the screen during the pressing test;

the processing the acquired chromaticity coordinates, so as to acquire a chromatic aberration between the test point with a maximum value of X or a maximum value of Y in the chromaticity coordinates and the test point with a minimum value of X or a minimum value of Y in the chromaticity coordinates includes processing, by a processor, the acquired chromaticity coordinates, so as to acquire the chromatic aberration between the test point with the maximum value of X or the maximum value of Y in the chromaticity coordinates and the test point with the minimum value of X or the minimum value of Y in the chromaticity coordinates; and the comparing the chromatic aberration with a predetermined standard chromatic aberration, so as to determine whether the screen is qualified after the pressing test includes comparing, by the processor, the chromatic aberration with the predetermined standard chromatic aberration, so as to determine whether the screen is qualified after the pressing test.

12. A device for determining a yellowish level of a screen caused by pressing, comprising:

an acquisition module, configured to acquire chromaticity coordinates of a plurality of test points of the screen during a pressing test;

a pressure application mechanism, configured to perform the pressing test on the screen, wherein a pressing end of the pressure application mechanism is made of optical abrasion-resistant glass;

a processing module, configured to process the acquired chromaticity coordinates, so as to acquire a chromatic aberration between the test point with a maximum value of X or a maximum value of Y in the chromaticity coordinates and the test point with a minimum value of X or a minimum value of Y in the chromaticity coordinates; and a determination module, configured to compare the chromatic aberration with a predetermined standard chromatic aberration, so as to determine whether the screen is qualified after the pressing test.

13. The device according to claim 12, wherein the acquisition module is further configured to:

select, prior to the pressing test, an odd number of test points which are equally-spaced, along a direction of a short side of the screen;

acquire initial chromaticity coordinates of the test points prior to the pressing test; and acquire, during the pressing test, the chromaticity coordinates of the test points every N thousands times the screen have been pressed, wherein N is a positive integer.

14. The device according to claim 13, wherein the processing module is further configured to:

plot a first comparison chart based on the values of X in the initial chromaticity coordinates of the plurality of the test points, or plot a first comparison chart based on the values of X in the chromaticity coordinates of the plurality of the test points after pressing the test points by identical times, wherein names of the test points are indicated by a horizontal axis of the first comparison chart, one coordinate unit represents a distance between two adjacent test points, and the values of X in the chromaticity coordinates of the test points are indicated by a vertical axis of the first comparison chart;

set the test point with the minimum value of X in the chromaticity coordinates in the first comparison chart as a first data point;

calculate first slopes of straight lines each connecting the first data point and a data point corresponding to the value of X in the chromaticity coordinates of the test point in the first comparison chart; and compare absolute values of the first slopes with each other, and set a maximum absolute value of the first slopes as the chromatic aberration between the test point with the maximum value of X in the chromaticity coordinates and the test point with the minimum value of X in the chromaticity coordinates.

15. The device according to claim 14, wherein the processing module is further configured to:

plot a second comparison chart based on the values of Y in the initial chromaticity coordinates of the plurality of the test points, or plot a second comparison chart based on the values of Y in the chromaticity coordinates of the plurality of the test points after pressing the test points by identical times, wherein names of the test points are indicated by a horizontal axis of the second comparison chart, one coordinate unit represents a distance between two adjacent test points, and the values of Y in the chromaticity coordinates of the test points are indicated by a vertical axis of the second comparison chart;

set the test point with the minimum value of Y in the chromaticity coordinates in the second comparison chart as a second data point;

calculate second slopes of straight lines each connecting the second data point and a data point corresponding to the value of Y in the chromaticity coordinates of the test point in the second comparison chart; and compare absolute values of the second slopes with each other, and set a maximum absolute value of the second slopes as the chromatic aberration between the test point with the maximum value of Y in the chromaticity coordinates and the test point with the minimum value of Y in the chromaticity coordinates.

16. The device according to claim 15, wherein the determination module is further configured to:

compare the maximum absolute value of the first slopes with the predetermined standard chromatic aberration, and determine that the screen is qualified after the pressing test in the case that the maximum absolute value of the first slopes is not greater than the predetermined standard chromatic aberration; and/or compare the maximum absolute value of the second slopes with the predetermined standard chromatic aberration, and determine that the screen is qualified after the pressing test in the case that the maximum absolute value of the second slopes is not greater than the predetermined standard chromatic aberration.

17. The device according to claim 13, wherein the processing module is further configured to:

plot a first comparison chart based on the values of X in the initial chromaticity coordinates of the plurality of the test points, or plot a first comparison chart based on the values of X in the chromaticity coordinates of the plurality of the test points after pressing the test points by identical times, wherein names of the test points are indicated by a horizontal axis of the first comparison chart, one coordinate unit represents a distance between two adjacent test points, and the values of X in the chromaticity coordinates of the test points are indicated by a vertical axis of the first comparison chart;

plot a parabola by connecting data points corresponding to the values of X in the chromaticity coordinates of the test points in the first comparison chart, so that each data point in the parabola has a corresponding curvature; and calculate a first curvature of the test point with the maximum value of X in the chromaticity coordinates, and setting the first curvature as the chromatic aberration.

18. The device according to claim 17, wherein the processing module is further configured to:

plot a second comparison chart based on the values of Y in the initial chromaticity coordinates of the plurality of the test points, or plot a second comparison chart based on the values of Y in the chromaticity coordinates of the plurality of the test points after pressing the test points by identical times, wherein names of the test points are indicated by a horizontal axis of the second comparison chart, one coordinate unit represents a distance between two adjacent test points, and the values of Y in the chromaticity coordinates of the test points are indicated by a vertical axis of the second comparison chart;

plot a parabola by connecting data points corresponding to the values of Y in the chromaticity coordinates of the test points in the second comparison chart, so that each data point in the parabola has a corresponding curvature; and calculate a second curvature of the test point with the maximal value of Y in the chromaticity coordinates, and set the second curvature as the chromatic aberration.

19. The device according to claim 18, wherein the determination module is further configured to:

compare the first or the second curvature with the predetermined standard chromatic aberration, and determine that the screen is qualified after the pressing test in the case that neither of the first and the second curvatures is greater than the predetermined standard chromatic aberration.

20. The device of claim 12 wherein:

the acquisition module is an optical test lens arranged to acquire the chromaticity coordinates of the plurality of test points of the screen during the pressing test; and the processing module and the determination module are a processor configured to process the acquired chromaticity coordinates, so as to acquire the chromatic aberration between the test point with the maximum value of X or the maximum value of Y in the chromaticity coordinates and the test point with the minimum value of X or the minimum value of Y in the chromaticity coordinates and further configured to compare the chromatic aberration with the predetermined standard chromatic aberration, so as to determine whether the screen is qualified after the pressing test.

* * * * *